United States Patent [19]

Bolza et al.

[11] 4,077,820
[45] Mar. 7, 1978

[54] GELLED-WATER BEARING EXPLOSIVE COMPOSITION

[75] Inventors: Frederick Bolza, Hawthorn East; Thomas Jellinek, Ripponlea; Keith Gordon Neill, Kew; Howard William Tankey, Box Hill North, all of Australia

[73] Assignee: ICI Australia Limited, Australia

[21] Appl. No.: 663,107

[22] Filed: Mar. 2, 1976

Related U.S. Application Data

[62] Division of Ser. No. 445,782, Feb. 25, 1974, abandoned.

[30] Foreign Application Priority Data

Mar. 19, 1973 Australia .............................. 2656/73
Dec. 20, 1973 Australia .............................. 6077/73

[51] Int. Cl.² ............................................. C06B 23/00
[52] U.S. Cl. .................................. 149/109.4; 149/41; 149/44; 149/60
[58] Field of Search .................. 149/44, 41, 60, 109.4

[56] References Cited

U.S. PATENT DOCUMENTS 3,940,297  2/1976  Bolza .............................. 149/44 X Primary Examiner—Jr. Lechert
Attorney, Agent, or Firm—Cushman, Darby & Cushman

[57] ABSTRACT

A gelled water-bearing explosive comprising a water-soluble oxygen releasing salt such as ammonium nitrate, a fuel, water and a gelling agent. The gelling agent is an organic metallic complex of a metal with a copolymer of a water-soluble monomer and a monomer which forms, with a metal, a chelate ring.

6 Claims, No Drawings

GELLED-WATER BEARING EXPLOSIVE COMPOSITION

This is a division of application Ser. No. 445,782 filed Feb. 25, 1974, now abandoned.

This invention relates to new compositions of matter comprising polymeric material. More particularly the invention relates to compositions of matter comprising copolymeric material of which at least a part is soluble in aqueous media and which is capable of acting as a thickening or gelling agent in such media. Such compositions are useful in a variety of industrial applications, thus for example they have been found to be extremely valuable in explosives technology, in the metal, mining, textile, cosmetic, pharmaceutical, horticultural and agricultural industries, and to a lesser extent in other industries, where there is a need for thickened or gelled water based products.

The use of naturally occurring gums as thickening agents for water bearing systems has long been known and more recently synthetic polymeric substances, for example polyacrylamide, have been used for the same purpose. In particular such gums and polymeric materials have been used to form water bearing gels.

Gel formation is particularly desirable when undissolved solids are present in a system and must be maintained in a relatively uniform state of dispersion therein. As used herein, a gel is a mixture, one component of which is water, homogeneous down to substantially colloidal dimensions and capable of resisting a finite shearing force. This resistance to shearing is evidence of some sort of continuous mechanical network or structure which, however, can constitute a relatively small fraction of the total mass of the composition of which the gel is a component. Thus the gel forms a matrix in which both dissolved and undissolved components can be distributed. Whilst the gums and polymers of the prior art have been reasonably satisfactory as agents for thickening or gelling water bearing systems they have sometimes been found to be deficient in that the degree of thickening or gelation has been hard to control or that in the instances where gels were formed such gels were physically weak and tended to rupture or in instances where electrolytes were present in the water bearing systems the gel structures were prone to collapse. Such deficiencies sometimes led to segregation of undissolved components in the system and furthermore often resulted in the desired product having a low degree of waterproofness.

We have now found new polymeric materials which, when used as thickening or gelling agents in water bearing systems, provide products wherein the deficiencies outlined above are reduced considerably and in some instances such deficiencies may be eliminated.

Accordingly we provide as a new composition of matter polymeric material characterized in that said polymeric material is soluble at least in part in an aqueous medium and comprises a synthetic polymer derived from a monomer which carries at least one group which is capable of reacting with a metal ion or which may be converted to a form capable of reacting with a metal ion.

Whilst it lies within our invention that the said polymeric composition may be a mixture of polymers it is preferred that the polymeric composition comprises copolymeric material.

Accordingly in an embodiment of our invention we provide a copolymeric composition of matter characterised in that the said copolymeric composition is soluble at least in part in an aqueous medium and comprises a synthetic polymer derived from a monomer which carries at least one group which is capable of reacting with a metal ion or which may be converted to a form capable of reacting with a metal ion. The copolymeric composition may be derived from a wide variety of monomers. Thus for example one of the polymeric constituents therein may be derived from unsaturated monomers such as acrylamide, vinyl pyrrolidone, vinyl alcohol, certain unsaturated acids such as methacrylic acid or derivatives thereof such as dimethylaminoethyl methacrylate and the like. Another of the polymers therein should be derived from monomers containing a group capable of reacting with metal ions. Suitably such a group is a chelating or chelate forming group, preferably a polydentate group and usually a bidentate group which contains two donor groups, said donor groups being so situated with respect to one another that they are capable of forming with a metal a chelate ring, preferably a chelate ring of five or six atoms. The donor groups are well known and recognized in chelate chemistry, the principal ones being listed at page 168 of the well known test "Chemistry of the metal chelate compounds" by Martell and Calvin published by PrenticeHall Inc., New York, 1952. The most important donor groups, and consequently the chelate-forming structures therefrom, are those which contain oxygen, sulphur or nitrogen as the donor atoms. In the language of chelate chemistry organic compounds containing chelating structures are called ligands and for the purpose of this invention it is necessary to use organic compounds which in their monomeric form have at least two ligand functions and therefore such compounds are often referred to herein as polyligands. From amongst groups which may be present in the monomers from which the metal reactive polymers may be prepared there may be mentioned groups such as carboxyl; sulphonyl; enolic hydroxyl and alcoholic hydroxyl; carbonyl; primary amino; secondary amino; tertiary amino; cyclic tertiary amino; thioether; imino; substituted imino; and thioalcohol.

As is known, some of these groups form covalent bonds and others form coordinate bonds with the metal which is part of the chelate rings. Chelates exist wherein the valences of the metal are all covalent, or all co-ordinate, or mixed. Mixed covalent and coordinate bonds are present in the most common chelates, and therefore it is in general preferred that the chelating structures of the polyligand be of such a type as to form chelates in which the metal is bonded to the adjacent atoms of the chelate ring through one covalent and one co-ordinate bond. Examples of chelating structures (or polydentate groups) include the following well-known ones, which can be attached to the rest of the polyligand molecule in any suitable manner, it being understood always that there are at least two chelating structures per polyligand molecule: beta-ketoacyloxy group, $\sigma$-hydroxy-benzoyl group, salicylate groups, alpha:-betadihydroxy substituted groups, $\alpha$: beta-dioxime group, thioacetic acid and esters and ethers thereof, alpha-aminosulphonic acid, 8-hydroxy-quinoline, $\sigma$-aminophenol, $\sigma$-nitrophenol, $\sigma$-aminothiophenol, ethylene diamine, alpha:beta-di-secondary amines of the type $RNH-CH_2-CH_2-NHR$, alpha:beta-ditertiary amines of the type $R_2N-CH_2-CH_2-NR_2$, alpha-betadithioethers of the type R—S—CH$_2$—CH$_2$—S—R, oxalyl group, alpha-hydroxyoxime group, beta-diketo group including the mono and dioximes, and salicylidenimino groups.

So as to exemplify monomers containing such polyligands it may be mentioned that copolymers prepared from specific monomers such as methacrylic hydrazide, acryloyliminodiacetic aicd, 5-alloyloxymethyl-8-quinolinol, N-formylamido acrylic acid; 4-cyclopentene 1,3-dione, diacetone acrylamide; 3-(2-hydroxy-3-naphthoyloxy) propyl acrylate; or (meth)acryloxymethylsalicylate have been found to be useful. Copolymers derived from methacryloyl acetone or 2-acetoacetoxyethylmethacrylate are particularly useful. Whilst for many purposes a satisfactory copolymer may be prepared from only two monomers, it lies within our invention to provide a copolymer derived from more than two monomers. Thus for example the use of two monomers not containing metal reactive groups in conjunction with one monomer containing a chelating group often provides a useful terpolymer for a specific purpose of thickening or gelling an aqueous medium. Alternatively terpolymers comprising two polymers derived from two monomers containing different metal reactive groups may sometimes be employed to advantage in controlling rates of thickening or gelation of water bearing systems.

We have also found that certain properties of a thickened or gelled water bearing system, for example the water resistance of such a system, may be enhanced if there is used as a thickening or gelling agent a water soluble or dispersible copolymeric material comprising a copolymer as hereinbefore described and a further polymer which is less water soluble than the copolymers hereinbefore described and which is derived from a monomer which is insoluble in water or soluble therein only to a slight extent say up to about 10% w/w.

Accordingly we provide in a further embodiment of our invention a copolymeric composition comprising a copolymeric composition of matter as hereinbefore described and comprising in addition a polymeric material which is less soluble in an aqueous medium than said copolymeric composition as hereinbefore described. The choice of the additional polymeric material in such compositions will of course be dictated by the nature and solubility of the copolymeric composition as hereinbefore described. Typical examples of monomers from which the additional polymer may be prepared include for example alkyl(meth)acrylates, vinyl acetate, vinyl propionate, vinyl pyridine, vinylidene chloride, styrene, acrylonitrile, alkyl vinyl ethers, allyl acetate, dialkyl maleates or dialkyl fumarates.

We have also found that the capability of thickening or gelling water bearing systems by naturally occurring materials or derivatives thereof is enhanced if such naturally occurring materials or derivatives are reacted with monomers capable of forming the copolymers of our invention.

Accordingly, we provide in yet another embodiment of our invention a water soluble or dispersible copolymeric composition of matter comprising a copolymeric composition of matter as hereinbefore described and comprising in addition a naturally occurring polymeric material or a derivative thereof capable of thickening or gelling a water bearing system. Such naturally occurring materials or their derivatives are well known and include for example hydrophillic gums such as the galactomannans of which guar gum and locust bean gum are typical examples. Other such materials include polysaccharides and carbohydrate derivatives such as the xanthan gums prepared by the microbal transformation of carbohydrate material. Typical examples of such derivatives are those products prepared from glucose by treatment with microorganisms of the genus *Xanthomonas* for example the plant pathogen *Xanthomonas campestris*. Further suitable derivatives of naturally occurring materials include water soluble derivatives of cellulose for example hydroxyethylecellulose.

The polymeric materials of our invention may be prepared by the well known processes whereby two or more monomers are reacted to form random, block or graft copolymers. Thus our copolymers may be prepared by reacting a first water soluble monomer with at least one further monomer which is characterized in that it carries a group which is capable of reacting with a metal ion or may be converted to a form capable of reacting with a metal ion. For example acrylamide may be reacted with methacryloyl acetone under polymerizing conditions to provide a copolymer of polyacrylamide and poly(methacryloyl acetone). The ratio of the individual polymers in the copolymer is merely a matter of choice dependent mainly on the purpose for which the copolymer is to be used but we have found that copolymers wherein the amounts of the polymer containing a group capable of reacting with a metal ion lie in the range up to 20% on a molar basis of the copolymer are very satisfactory when used as thickening or gelling agents in water based systems. Similarly terpolymers may be prepared. Thus for example acrylamide, methacryloyl acetone and a third monomer such as acrylonitrile or methylmethacrylate may be copolymerized. The amount of polymer derived from the said third monomer is not narrowly critical except in so far as it should not be of such a proportion that the terpolymer is insoluble in the water based system in which it is being used and we have found that satisfactory terpolymers are obtained when the polymeric component derived from the third monomer is present in the terpolymers in an amount up to 25% on a molar basis of the terpolymer.

In an alternative method of preparation of our compositions a performed water soluble polymer of either a synthetic or naturally occurring type may be reacted with a monomer or compound containing a group capable of reacting with a metal. Thus for example a chelating group attached to a functional group in a compound may be reacted with a water soluble polymeric material. This type of preparation may be typified by the transesterification of a water soluble copolymer of N-vinylpyrollidone and hydroxyethyl methacrylate with ethyl acetoacetate. Naturally occurring materials such as starch or guar gum may also be modified by suitable processes to form compositions according to our invention. Thus for example a mixture of acrylamide and methacryloyl acetone may be cografted on to the natural polymer to provide a graft copolymer.

As indicated above the polymeric compositions of our invention are suitable for thickening water bearing compositions and accordingly we provide a water bearing composition comprising an amount of a polymeric composition according to our invention sufficient to increase the viscosity of said water bearing composition. The amount of the polymeric composition used for any particular purpose may suitably be determined by simple experimentation. In instances where only a small increase in the viscosity of a water bearing composition is desired amounts of copolymer up to about 3% of the total weight of the composition are suitable; but larger amounts, say up to about 10% may be used if desired. The degree of thickening by an amount of copolymer is also influenced to some extent by the molecular weight of the copolymer used. Thus polymeric material of a relatively low molecular weight, say of the order of 10,000 to 200,000, will provide products which are less viscous than one wherein an equal weight of a copolymer is used and wherein the molecular weight of the polymeric material is 1,000,000 or even higher. Such high molecular weight polymers are preferred for many purposes since they provide relatively more viscous solutions per unit weight of copolymer used.

In addition to their capability to increase the viscosity of water bearing compositions, the polymeric compositions of matter according to our invention comprising at least one group capable of reacting with a metal ion also form metal complexes. Such metal complexes are new and accordingly we provide metal complexes wherein the organic component thereof is derived from a copolymer according to our invention. The metal component of such complexes will be dependent on the nature of the metal reactive group in the copolymer but in some cases a range of complexes can be obtained wherein the metallic component is different. We have found that such metal complexes may be prepared by reacting a water soluble copolymer of our invention with an aqueous solution of an appropriate metal salt. Such a reaction is conveniently performed at ambient temperatures although higher or lower temperatures may be used if desired. From amongst the range of metals which form metal complexes when reacted with our copolymers there may be mentioned water soluble compounds derived from zinc, cerium, aluminum, uranium, titanium, zirconium, lead, tin, vanadium, chromium, manganese or iron. Complexes comprising chromium are very useful.

The above metal derivatives of the copolymers of our invention have been found to be useful agents for gelling water bearing systems particularly such systems containing an electrolyte. By suitable choice of copolymer and metal salt we hve prepared a range of gels derived from water bases systems wherein the gels are formed over differing periods of time ranging from a few seconds to several weeks after the addition of a copolymer and a metal salt to the water bearing system. Accordingly we provide a gel, as hereinbefore defined, of a water bearing system, preferably a system containing an electrolyte, characterized in that said gel comprises a metal complex derived from a copolymeric coposition of matter according to out invention. The amount of the metal complex used in the preparation of the above gel will depend to some extent on the degree of gelation which is desired and to some extent on the nature of the water bearing system and the type of metal complex being used. For many purposes useful gels are obtained when the amount of metal complex in the system being treated is in the range from 0.1 to 10% w/w more usually from 0.5 to 5% w/w, of the total weight of the system being treated and the metal complex. The metal complexes described above are especially useful for the preparation of gels in water bearing systems comprising inorganic salts for example oxygen releasing salts such as ammonium nitrate, sodium nitrate or calcium nitrate. Thus they are particularly suitable for making explosive compositions such as gelled aqueous blasting agents. Such agents are easier to prepare in so far as the gelling agent is water soluble and does not require to be hydrated as in the instance of the gelled aqueous blasting agents, often referred as explosive slurries, of the prior art. Accordingly in a still further embodiment of our invention we provide a gelled water bearing explosive composition comprising at least one water soluble inorganic oxygen releasing salt; water; at least one fuel; and a gelling agent comprising at least one metal complex derived from a metallic compound and copolymeric material according to our invention.

In general, except for the gel matrix, such waterbearing explosives are of conventional types.

The oxygen releasing salts suitable for use in explosive compositions comprising gelling agents derived from our copolymeric compositions are of the conventional types used in explosive compositions. Thus they may be, for example, inorganic nitrates, chlorates and perchlorates and mixtures thereof. We prefer that the oxygen releasing salt material be chosen from the nitrates of the alkali and alkaline earth metals or ammonium and of these we prefer sodium nitrate, calcium nitrate and ammonium nitrate. The amount of oxygen releasing salt in such compositions is not narrowly critical; we have found that compositions containing amounts of oxygen releasing salts from 50% w/w to 90% w/w of the total composition are satisfactory and amounts from 65% w/w to 85% w/w are preferred. The particle size and shape of the oxygen releasing salt is not critical and is well known from the art of ammonium nitrate manufacture; powders and prilled particles are satisfactory.

The proportion of water in such compositions should be sufficient to dissolve at least part of the oxygen releasing inorganic salt and at least part of any water soluble fuel which may be present. Suitably the amount of water present may constitute from 5% w/w to 35% w/w of the total composition, but the amount present should not be in excess of the explosive limit of the composition. We prefer that the amount of water be in the range from 5% w/w to 25% w/w of the total composition and more preferably be in the range from 8% w/w to 17% w/w of the total composition.

When referring to fuels or fuel materials in these gelled compositions we mean substances which are stable in such explosive compositions, that is prior to detonation, during preparation and storage the substance is chemically inert to the system. The said substances must be combustible and their physical nature should be such that they may be incorporated in our compositions in a manner so as to be uniformly distributed throughout the compositions. Such fuels are well known in the art and they may be organic or inorganic and may also be derived from animals and plants.

The fuels emmployed in the compositions prepared by the process of this invention can be, for example, self-explosive fuels, non-explosive carbonaceous, non-metallic and metallic fuels or mixtures of the aforementioned types of fuels. They can be varied widely. Examples of self-explosive fuels include one or more organic nitrates, nitrocompounds and nitramines such as trinitrotoluene, cyclotri (or tetra) methylenetri (or tetra) nitramine, tetryl, pentaerythritol tetranitrate, explosive grade nitrocellulose and nitrostarch.

The self-explosive fuel can be for example in any of the well known flake, crystalline or pelleted forms. In general up to 35% and preferably from 10 to 30% by weight based on the weight of composition of self-explosive fuel may be used.

Suitable water soluble fuels are organic water soluble substances for example urea, carbohydrates such as sugars or molasses, water soluble alcohols or glycols, glues or mixtures of these. Suitably the proportion of water soluble fuel in such explosive compositions is in the range from 0.8% w/w to 20% w/w of the total composition. Amounts from 4% w/w. to 7% w/w of the total composition are preferred.

Suitably water insoluble or sparingly water soluble fuels may be chosen from inorganic materials for example sulphur, aluminium, silicon, ferrosilicon, ferrophosphorus, magnesium, titanium, boron, mixtures thereof for example mixtures of aluminum with ferrosilicon, or organic materials for example finely divided charcoal, anthracite, gilsonite, asphalt, fuel oil, cellulosic materials such as sawdust, or cereal products for example flours, dextrins or starches. When the inorganic fuel is a metal it is preferably in granulated or powdered from ranging in particle size from coarse, for example retained on a 30 mesh sieve, to very fine for example passing a 325 mesh sieve. Such granulated or powdered metal may be in the form of discrete regular shaped particles, but metal powder wherein the metal is in the form of irregular shaped particles, or in flakes or in the form of aggregates of particles or flakes are also satisfactory. Preferred fuels are the metallic owders. The most preferred metallic fuel is aluminum. The proportion of water insoluble or sparingly water soluble nonmetallic fuels in such compositions may suitably be in the range from 1% w/w to 10% w/w of the total composition and amounts from 4% w/w to 7% w/w of the total compositions are preferred. The proportion of metallic water insoluble fuels when present in such compositions may be as high as 25% w/w and amounts in the range from 0.5% w/w to 20% w/w of the total compositions are preferred.

Where desirable, it is convenient to add to the slurry explosive compositions described above, in amounts expressed as parts by weight per 100 parts by weight of the final mixture, other conventional additives used in slurry explosives. Such additives may include for example anti-foaming agents, for example ethyl hexanol, in amounts ranging e.g. from 0 to 0.1 part, surfactants, for example non-ionic surfactants such as alkylene oxide condensates of phenols or amides, from 0 to 5 parts. When desired, sensitizers in the form of gas or a mixture of gases such as air may be added to such compositions. Thus it may be added in the form of injected or stirred in air or gas or it may be added as air or gas encapsulated in or attached to the surface of particulate material. Alternatively a gas, such as nitrogen or carbon dioxide, may if desired be generated in the composition by known means. Yet again further sensitizers in the form of modified metallic powders may be added to the explosive compositions. Such modified metallic powders include for example the reaction product of aluminum powder with resin acids, rosin or derivatives thereof. If desired there may also be added to the explosive compositions additional gelling agents already known in the prior art. Such explosive compositions may be prepared by conventional means. Thus for example it is convenient to prepare a premix of the oxygen releasing salts and water insoluble fuels if such fuels are used. To this premix there may then be added an aqueous solution comprising the bulk of the water in which any water soluble fuels, if used, and the copolymer material according to our invention had been predissolved so as to form a mixture. An aqueous solution of the metallic compound in the remainder of the water may then be added to and admixed with the mixture described above, so as to form a gelled product. The proportion of the gelling agent in such explosives compositions may conveniently be in the range from 0.1 to 5% w/w, more usually from 0.2 to 3% w/w, of the composition. Such compositions comprising our gelling agents are easier to prepare than similar compositions of the prior art since the components of the gelling agent are water soluble and are generated in situ to form a matrix. Unlike prior art compositions using, for example, guar gum, no prehydration of the gelling agents is necessary. Additionally the explosive compositions as described above are markedly superior to prior art compositions in resistance to degradation during storage and in resistance to leaching of the components when the compositions are in contact with aqueous media, for example when in contact with water in a borehole when in processes of blasting and have thus enabled improvements to be made in blasting processes. By means of the use of explosive compositions described above it is now possible to perform blasting operations in areas where hitherto because of the presence of water in such areas, it has been difficult to detonate explosive compositions of a similar type. Since the copolymeric compositions of our invention provide a means whereby water bearing explosive compositions may be converted to a highly stable gel form, they are extremely useful for preparing gelled explosives which may be packaged and conveniently used in small diameter boreholes in blasting operations.

Our invention is now illustrated by, but in no way limited to, the following examples in which all parts and percentages are on a weight basis unless otherwise stated. Example 40 is comparative and outside our invention.

EXAMPLE 1

Into a reaction vessel fitted with a reflux condenser, a gas inlet and outlet port, stirring means nd heating means there was added acrylamide (532 parts), methacryloyl acetone (13 parts), water (800 parts), an aqueous 30 % solution of ammonia (13 parts), an anqueous 0.25% solution of copper sulphate (11 parts) and an aqueous 10% solution of ammonium sulphate (60 parts). The components were stirred and heated to 65° C after which a stream of carbon dioxide was bubbled through the mixture for 15 minutes and this was followed by a stream of nitrogen for a similar time. An aqueous 2% solution of ammonium persulphate (8 parts) was added to the stirred mixture and stirring was continued for 30 minutes during which time the viscosity of the mixture increased. Water (3500 parts) was then added to the stirred mixture at a rate of 30 parts per minute to provide an aqueous solution of a copolymer containing polyacrylamide and poly(methacryoyl acetone).

The methacryloyl acetone used in this example was prepared as follows: — Sodamide (84 parts) and anhydrous diethyl ether (640 parts) were refluxed for one hour and then cooled to room temperature. A mixture of acetone (108 parts) and diethyl ether (108 parts) was then added over a period of 5 minutes followed by the addition of a mixture of methylmethacrylate (90 parts) and diethylether (108 parts). The resultant mixture was then refluxed with stirring for 2 hours. The resultant reaction mixture stood for 16 hours at room temperature and was then poured into a mixture of concentrated hydrochloric acid (165 parts) and ice (900 parts) and the ether layer was separated therefrom. The ether layer was washed with a 5% sodium bicarbonate aqueous solution (1000 parts) and then washed with water (1000 parts). The washed ether layer was dried over anhydrous sodium sulphate then distilled and then fractionated under reduced pressure. The fraction boiling at 57° C at a pressure of 3mm Hg was identified by elemental analysis, infrared spectroscopy and nuclear magnetic resonance as being methacryloyl acetone.

EXAMPLE 2

The general procedure of Example 1 was repeated but in the present example there was included, as an additional raw material monomer, acrylonitrile (10 parts). There was thus obtained an aqueous solution of a terpolymer containing polyacrylamide, poly(methacryloyl acetone) and polyacrylonitrile.

EXAMPLE 3

This example demonstrates the ability of our copolymers to act as a thickening agent. To 99 parts of water there was added 1 part of a copolymer of polyacrylamide, poly(methacryloyl acetone) and poly(methyl methacrylate) in a molar ratio of 88.5:0.5:11. The mixture was stirred and the resultant solution was found to have a viscosity of 130 centipoise at 22° C as measured by a Brookfield viscometer. Under similar conditions a 3% solution of a copolymer of polyacrylamide, poly(methacryloyl acetone) and polyacrylonitrile in a molar ratio of 100:10:5 in water had a viscosity of 126 centipoise.

EXAMPLES 4 to 18 inclusive

In these examples there is demonstrated the gelation of an aqueous solution containing an electrolyte by treatment thereof with a copolymer according to our invention and a metal compound. In the general method used there was added to 100 parts of an aqueous solution of ammonium nitrate or a mixture of ammonium and sodium nitrate, 10 parts of an aqueous solution containing 1.5 parts of a copolymer according to our invention. To the resultant mixture then was then added 0.1 part of a metallic compound dissolved in 0.9 parts of water and the whole was then agitated so as to form a homogeneous gelled mixture. In Table 1 the copolymer A was a copolymer of polyacrylamide and poly(methacryloyl acetone) in a molar ratio of 97.5:2.5; copolymer B was a terpolymer of polyacrylamide, poly(methacryloyl acetone) and polyacrylonitrile in a molar ratio 100:2.5:2.5; and copolymer C was a terpolymer of polyacrylamide, poly(methacryloyl acetone) and polymethylmethacrylate in a molar ratio of 87:3:10. In each of the examples the aqueous solution which was treated contained 60 parts of ammonium nitrate and 40 parts of water. In Example 6 5 parts of sodium nitrate was also present in the treated aqueous solution. Table 1 sets out the metal compounds used and includes comments on the gel formation.

TABLE 1

| Example No. | Co-polymer used | Metal compound used | Time to form a gel after addition of metal compound |
|---|---|---|---|
| 4 | A | CrCl$_3$6H$_2$O | 30 seconds. Firm gel after 15 minutes. |
| 5 | A | FeCl$_3$ | Within 5 seconds. |
| 6 | C | CrCl$_3$6H$_2$O | 25 seconds. Firm gel after 15 minutes |
| 7 | A | FeCl$_2$ | 2 hours. |
| 8 | A | ZrOCl$_2$ | 1 to 5 seconds. |
| 9 | A | VOSO$_4$ | 1 to 5 seconds. |

TABLE 1-continued

| Example No. | Co-polymer used | Metal compound used | Time to form a gel after addition of metal compound |
|---|---|---|---|
| 10 | A | (NH$_4$)Ce(NO$_3$)$_6$ | 4 hours. |
| 11 | A | Na$_2$Cr$_2$O$_7$ | 2 weeks. |
| 12 | B | KMnO$_4$ | Within 1 minute. |
| 13 | C | Al(NO$_3$)$_3$ | Within 1 minute. |
| 14 | A | Pb(O . COCH$_3$)$_2$ | 5 hours. |
| 15 | A | SnCl$_2$2H$_2$O | 2 weeks. |
| 16 | A | SnCl$_4$2H$_2$O | Within 1 minute. |
| 17 | A | ZnCrO$_4$ | Within 1 minute. |
| 18 | A | UO$_2$(OCOCH$_3$)$_2$ | Within 1 minute. |

EXAMPLE 19

A gelled blasting agent composition was prepared from the following components.

| | | |
|---|---|---|
| Ammonium nitrate prills | 660 | parts |
| Sodium nitrate | 30 | parts |
| Aluminium powder | 100 | parts |
| Sugar | 50 | parts |
| Water | 144.5 | parts |
| Copolymer B of Example 12 | 15 | parts |
| Chromic chloride | 0.5 | part |

A dry premix of the ammonium nitrate, sodium nitrate and aluminum powder was prepared. To this premix there was added a solution in which the copolymer and the sugar were dissolved in 140 parts of water and the resultant mixture was agitated until it was a uniform mass, whereupon the chromic chloride dissolved in the remainder of the water was added to the agitated mixture and agitation and mixing thereof was continued for a further 30 seconds. The composition was converted to a gel from within about one minute after the chromic chloride solution had been added. The product so obtained was stored at ambient temperature, 16° to 40° C, for two weeks during which time neither segregation of components nor syneresis was observed in the composition. The resistance to leaching by water of the water soluble components from the composition was tested by the following procedure. An amount of the composition which had gelled for 24 hours and containing 10 grams of ammonium nitrate was placed in a mesh basket and suspended in 200 ml of water at room temperature. After 75 minutes the basket and its residual content was removed from the aqueous medium. The aqueous medium was then stirred until it was homogeneous and a 50 ml aliquot taken therefrom was analysed for its ammonium nitrate content. The above procedure was repeated with the gelled composition after gelation had proceeded for each of 1 weak and 2 weeks. The percentage of the ammonium nitrate retained in the treated composition was as follows:

| | |
|---|---|
| After 24 hours gelation | 44% |
| After 1 week gelation | 38% |
| After 2 weeks gelation | 27% |

The above values demonstrate an enhanced resistance to water leaching when compared with the results obtained by treating a similar prior art composition which had been gelled by means of a crosslinked guar gum/zinc chromate agent and wherein 28%, 23% and 23% of ammonium nitrate was retained after 24 hours, 1 week and 2 weeks gelation respectively.

EXAMPLE 20

Using the general procedure of Example 19 there was prepared a mixture containing ammonium nitrate 6000 parts, sodium nitrate 1070 parts, water 1355 parts, sugar 450 parts, sulphur 300 parts, aluminum powder 700 parts, gilsonite 100 parts and copolymer A of Example 4 100 parts. A solution was prepared by dissolving 5 parts of chromic chloride in 20 parts of water. Using the apparatus described in Examples 1 and 3 of Belgian Pat. No. 778,210 and the method of Example 4 of the same patent the mixture described above was pumped at a rate of 70 lb/minute through a loading hose to an attached interfacial surface generator mixer. The chromic chloride solution was pumped at the rate of 150 ml/minute and injected into the said mixture just before the latter passed out of the loading hose and through the interfacial generator mixer. The explosive composition so formed was thus located in a borehole in the form of a stiff cohesive gel which was detonated successfully four hours later.

EXAMPLES 21 to 27 inclusive

These examples demonstrate the excellent resistance of a slurry explosive composition to leaching by water when a gelling agent derived from a copolymer of our invention and a water soluble metal salt is formed in situ in such a composition.

In each example a mixture of ammonium nitrate (655 parts), sodium nitrate (30 parts), aluminum powder (100 parts), sugar (50 parts) and water (65 parts) was prepared. Into this mixture ther was then uniformly incorporated a solution of the appropriate type of copolymer, as listed in Table 2, and in an amount as listed in Table 3, dissolved in 90 parts of water. There was then added to and uniformly admixed with the resultant mixture a solution of the appropriate amount and type of metal salt, as listed in Table 3, dissolved in 10 parts of water. The resultant gelled composition was then tested at intervals as set our in Table 3 for resistance to leaching by water using the method described in Example 19 and the results obtained are set out in Table 3. The copolymers used are as follows:

TABLE 2

| Copolymer designation | Molar ratio and type of polymeric component | | |
|---|---|---|---|
| | Polyacrylamide | Poly(methacryloylacetone) | Poly(methylmethacrylate) |
| A | 97.5 | 2.5 | — |
| C | 87 | 3 | 10 |
| D | 99 | 1 | — |
| E | 100 | 5 | 30 |
| F | 88.5 | 0.5 | 11 |

TABLE 3

| Example No. | Copolymer designation | Amount of copolymer used (parts) | Type of metal salt used | Amount of metal salt used (parts) | % ammonium nitrate retained after: | | |
|---|---|---|---|---|---|---|---|
| | | | | | 24 hrs | 1 week | 2 weeks |
| 21 | A | 50 | Ferric chloride | 2 | 36 | — | — |
| 22 | A | 51 | chromic chloride | 2 | 47 | — | — |
| 23 | C | 10 | chromic chloride | 0.25 | 49 | 47 | 49 |
| 24 | C | 6 | chromic chloride | 0.25 | 51 | 43 | 36 |
| 25 | D | 7.5 | chromic chloride | 1 | 44 | 38 | 27 |
| 26 | E | 15 | chromic chloride | 0.5 | 37 | 46 | 32 |
| 27 | F | 15 | chromic chloride | 1 | 36 | 26 | — |

"—" in the table indicates that no resistance test was made at the appropriate time.

EXAMPLE 28

A solution was prepared by dissolving 60 parts of ammonium nitrate in 40 parts of water. The viscosity of this solution was 16 centipoise at 22° C as determined by means of a Brookfield viscometer. 3 parts of a copolymer of polyacrylamide, poly(methacryloyl acetone) and polyacrylonitrile in a molar ratio of 100:10:5 was dissolved in the above solution to provide a thickened solution having a viscosity of 206 centipoise at 22° C.

EXAMPLE 29

In a mixing device conventionally used for preparing explosive compositions there was prepared a first mixture consisting of ammonium nitrate 1092 parts; calcium nitrate 1390 parts; thiourea 88 parts; water 317 parts; ethylene glycol 478 parts and copolymer B of Example 12 34 parts. Into this first mixture there was incorporated a second mixture consisting of gilsonite 6 parts; pregelled starch 40 parts; finely divided aluminum powder, the bulk of which passed through a 325 mesh sieve, 40 parts; and a coarser aluminum powder, the bulk of which was of particle size in the range from 20 to 150 mesh, 120 parts. The resultant blend was transferred to a cartridging device fitted with a stirrer, an inlet port, an outlet port and a piston. A tube of circular cross section having a length of 12 inches and a diameter of 1 inch, and closed at one end and fabricated from a film comprising polyethylene terephthalate was positioned so that its open end was placed over the outlet port referred to above. The blend was agitated and a solution of 0.5 part of chromic chloride in 4.5 parts of water was added to the blend through the inlet pport of the device. Upon addition of the chromic chloride solution the blend was converted rapidly to a gelled from which was extruded by means of the piston through the outlet port into the plastic tube. The filled tube was then removed from the outlet port and the open end of the tube was closed. In the manner described above a multiplicity of packaged explosive compositions was prepared. These packaged compositions were stored at ambient temperature for one week during which time the contents of the packages became increasingly firm. The cartridged explosive so obtained was then detonated successfully by conventional means in a borehole made in a quarry.

EXAMPLE 30

This example illustrates a process whereby a solution of a copolymer containing 97 molar parts of polyacrylamide and 3 molar parts of poly (2-acetoacetoxyethylmethacryylate) may be prepared.

Into a reaction vessel fitted with a reflux condenser, a gas inlet and outlet port and stirring means there was charged acrylamide (276 parts), 2-acetoacetoxyethyl methhacrylate (26 parts), water (500 parts) and an aqueous 10% solution of ammonium sulphate (25 parts). These materials were mixed by stirring to form a solution which was then diluted by the addition of water (3200 parts). A stream of nitrogen gas was passed through the stirred mixture for 30 minutes and an inert atmosphere was maintained in the reaction vessel. To the stirred mixture at a temperature of 21° C there was then added 8 parts of an aqueous solution of ammonia (specific gravity 0.90) followed by 15 parts of an aqueous 1% solution of ammonium persulphate. After these additions were made stirring was continued for 35 minutes and the reaction mixture was then stored for 12 hours during which time the temperature of the reaction mixture reached a maximum of 34° C. There was thus obtained an aqueous solution of a copolymer of polyacrylamide and poly (2-acetoacetoxyethylmethacrylate).

The 2-acetoacetoxyethylmethacrylate used in this example was prepared as follows : Into a reaction vessel fitted with stirring means and cooling means there was charged 650 parts of benzene, 680 parts of β-hydroxyethylmethacrylate, 19 parts of sulphur and 3 parts of triethylamine. To this stirred mixture there was added in a dropwise fashion 700 parts of diketene. During the above addition of diketene the temperature of the reaction mixture was below 70° C. After the addition of diketene was completed the temperature of the stirred reaction mixture was adjusted to 60° C and this temperature was maintained for 30 minutes. The reaction mixture was then filtered and benzene was removed from the filtrate by distillation. The resulting residue was distilled fractionally under reduced pressure. The fraction of the distillate which had a boiling range of from 97° to 100° C at a pressure of 0.5 mm Hg was separated from the remainder of the distillate. By means of elemental analysis, infrared spectroscopy and nuclear magnetic resonance this separated fraction was identified as being essentially 2 -acetoacetoxyethylmethacrylate.

EXAMPLE 31

This example illustrates a process whereby a terpolymer containing 94 molar parts of polyacrylamide, 3 molar parts of poly (2-acetoacetoxyethylmethacrylate) and 3 molar parts of polyacrylonitrile may be prepared.

Into a reaction vessel fitted with a reflux a gas inlet and outlet port and stirring means there was charged acrylamide (222 parts), 2-acetoacetoxyethylmethacrylate (21 parts), acrylonitrile (5 parts) and water (500 parts). These materials were mixed to form a solution and an aqueous 10% solution of ammonium sulphate (25 parts) and water (2750 parts) were then added to the solution and incorporated therein by the stirring means to form a mixture. A stream of nitrogen gas was passed through the stirred mixture for 30 minutes and an inert atmosphere was maintained in the reaction vessel. To the stirred mixture at a temperature of 23° C there was then added 10 parts of an aqueous solution of ammonia (specific gravity 0.90), followed by 15 parts of an aqueous 1% solution of ammonium persulphate. After these additions were made stirring was continued for 35 minutes and the reaction mixture was then stored for 12 hours during which time the temperature of the reaction mixture reached a maximum of 35° C. There was thus obtained an aqueous solution of a terpolymer of polyacrylamide, poly (2-acetoacetoxyethylmethacrylate) and polyacrylonitrile.

EXAMPLE 32

Into a reaction vessel fitted with a reflux condenser, a gas inlet port, a gas outlet port, stirring means and heating means there was charged 150 parts of water, 10 parts of a partially hydrolysed polyvinyl acetate available commercially under the Registered Trade Name of "Gelvatol" 20/90, 30 parts of acrylamide and 2.2 parts of 2-acetoacetoxyethylmethacrylate and these components were then stirred for 30 minutes whilst a stream of nitrogen gas was passed through the mixture to provide an inert atmosphere in the reaction vessel. The contents of the vessel were heated to a temperature of 40° C and 10 parts of a 0.1m aqueous solution of ammonium ceric nitrate were added to the vessel and mixed with the other components by stirring for 30 minutes. The product was cooled to room temperture and there was thus obtained an aqueous composition containing a polymeric material comprising a partially hydrolysed polyvinyl acetate with which has been polymerized a copolymer derived from acrylamide and 2-acetoacetoxyethylmethacrylate.

EXAMPLE 33

A portion of the aqueous compositions obtained in Example 32 was diluted with water to provide 5% aqueous solution of the polymeric material. To 30 parts of this solution there was added with stirring 10 parts of a 10% aqueous solution of $ZrOCl_2$ and it was observed that a gelled product was obtained rapidly.

EXAMPLE 34

Using the apparatus of Example 32 5 parts of guar gum were dispersed and hydrated in 250 parts of water. To this stirred dispersion there was added 30 parts of acrylamide and 2.2 parts of 2-acetoacetoxyethylmethacrylate and the resultant dispersion was stirred for 30 minutes whilst a stream of nitrogen gas was passed through the dispersion which was concurrently heated to a temperature of 40° C. 5 parts of a 0.1M aqueous solution of ammonium ceric nitrate were added to the vessel and mixed with the other components by stirring for 30 minutes. The product was cooled to room temperature and there was thus obtained an aqueous composition containing a polymeric material comprising guar gum with which had been polymerized a copolymer derived from acrylamide and 2-acetoacetoxy ethylmethacrylate.

EXAMPLE 35

A portion of the aqueous composition obtained in Example 34 was diluted with water to provide a concentration of 3.7% of the polymeric material. To 20 parts of the diluted composition there was added 10 parts of a 10% aqueous solution of lead nitrate. The mixture was stirred for 5 minutes and then allowed to stand at room temperature for 24 hours during which time the resultant composition was converted to a soft gel form.

EXAMPLE 36

Using the apparatus of Example 32 a stirred mixture of 75 parts of water and 27.2 parts of N-vinylpyrrolidone was heated to a temperature of 55° C. A stream of nitrogen gas was then passed through the mixture for 20 minutes and 0.15 part of azobisisobutyronitrile was then added and stirring was continued. After 20 minutes there was commenced the addition of a solution containing 1.1 parts of 2-acetoacetoxyethylmethacrylate dissolved in 10 parts by volume of a 1 : 1 mixture of water and methanol. The addition of the solution was adjusted to a steady rate such that the solution was dispensed over a period of three hours. The resultant contents of the reaction vessel were stirred for a further 30 minutes and then cooled to room temperature. There was thus obtained a solution of a copolymer derived from N-vinylpyrrolidone and 2-acetoacetoxyethylmethacrylate the said copolymer comprising about 17% of poly(2-acetoacetoxyethylmetharcylate).

EXAMPLE 37

A portion of the aqueous composition obtained in Example 36 was diluted with water to provide a concentration of 5% of the polymeric material. To 20 parts of the diluted composition there was added 10 parts of a solution formed from 9 parts of water and 1 part of stannic chloride. The resultant mixture was stirred and allowed to stand for 30 minutes during which time the mixture was converted to a gel form.

EXAMPLE 38

The general procedure of Example 29 was repeated except that the first mixture consisted of 3600 parts of ammonium nitrate prills, 1100 parts of sodium nitrate, 300 parts of sugar, 344 parts of water and 606 parts of an aqueous solution prepared from the solution of the copolymer obtained in Example 30 and containing 40 parts of the copolymer described in Example 30; whilst the second mixture consisted of 2600 parts of powdered ammonium nitrate, 800 parts of aluminum powder the bulk of which passed through a 200 mesh sieve, 350 parts of wood meal, and 200 parts of finely divided aluminum powder the bulk of which passed through a 325 mesh sieve; and the solution of chromic chloride consisted of 10 parts of chromic chloride dissolved in 90 parts of water. There was thus obtained a multiplicity of packaged explosive compositions which were stored at ambient temperature for one week during which time the contents of the packages became increasingly firm. The cartridged explosive so obtained was then detonated successfully by conventional means in a borehole made in a quarry.

EXAMPLE 39

The general procedure of Example 29 was repeated except that the first mixture consisted of 3600 parts of ammonium nitrate prills, 1100 parts of sodium nitrate, 200 parts of sugar and 1100 parts of an aqueous solution prepared from the solution of the terpolymer obtained in Example 31 and containing 80 parts of the terpolymer described in Example 31; whilst the second mixture consisted of 2625 parts of powdered ammonium nitrate, 1000 parts of gilsonite, 800 parts of aluminum powder the bulk of which passed through a 200 mesh sieve, and 100 parts of pregelled starch; and the solution of chromic chloride consisted of 20 parts of chromic chloride dissolved in 180 parts of water. There was thus obtained a multiplicity of packaged explosive compositions which during storage at ambient temperatures became increasingly firm. After being stored for one week the cartridges were detonated successfully by conventional means in boreholes in rock during a tunnelling operation. When the explosive composition of the present example was examined for resistance to leaching by water, as determined by the procedure set out in Example 19, after two weeks of storage it was found that 35% of the ammonium nitrate was retained in the treated composition.

Example 40

For the purposes of comparison the general procedure of Example 24 was repeated except that in the present example the 6 parts of copolymer C used in Example 24 was replaced by 8 parts of a commercially available polyacrylamide, and the amount of chromic chloride was increased to 0.5 part. There was thus obtained after 24 hours reaction time a rubbery composition. It was observed that crosslinking within the composition was not uniform and furthermore that after storage at ambient temperature for two weeks it was apparent that syneresis and segregation of the aluminum powder had occurred in the composition and that the gelled product had deteriorated. When tested for resistance to leaching by water the following results were obtained.

| | |
|---|---|
| Ammonium nitrate retained after 24 hours | 35% |
| Ammonium nitrate retained after 4 days | 31% |
| Ammonium nitrate retained after 2 weeks | 19% |

We claim:

1. A gelled water-bearing explosive composition comprising at least one water soluble inorganic oxygen releasing salt, at least one fuel, from 5 to 35% by weight of water; and 0.1 to 5% by weight of a gelling agent comprising an organic metallic complex of a metal selected from the group consisting of zinc, cerium, aluminum, uranium, titanium, zirconium, lead, tin, vanadium, chromium, manganese and iron, and a copolymer of a water-soluble monomer and a monomer containing a bidentate group which contains two donor groups which forms with a metal, a chelate ring.

2. A gelled explosive composition according to claim 2 wherein the copolymer comprises up to 20 molar percent of the monomer containing a bidentate group.

3. A gelled explosive composition according to claim 1 wherein the monomer containing a bidentate group comprises methacryloyl acetone or 2-acetoacetoxyethyl methacrylate.

4. A gelled explosive composition according to any one of claim 1 wherein the water soluble monomer comprises acrylamide, vinyl pyrrolidone, vinyl alcohol, methacrylic acid or dimethylaminoethyl methacrylate.

5. A gelled explosive composition according to claim 1 wherein the copolymer is derived from a further monomer comprising an alkyl methacrylate or acrylonitrile in addition to the water soluble monomer and the monomer containing the bidentate groups.

6. A gelled explosive composition according to claim 1 wherein the metal is chromium.

* * * * *